(12) United States Patent
Behkish et al.

(10) Patent No.: US 11,130,718 B2
(45) Date of Patent: Sep. 28, 2021

(54) OXYGENATE CONVERSION FOR DISTILLATE FUEL PRODUCTION

(71) Applicant: ExxonMobil Research and Engineering Company, Annandale, NJ (US)

(72) Inventors: Arsam Behkish, Flemington, NJ (US); Anjaneya S. Kovvali, Herndon, VA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 0 days.

(21) Appl. No.: 16/909,999

(22) Filed: Jun. 23, 2020

(65) Prior Publication Data

US 2020/0399190 A1 Dec. 24, 2020

Related U.S. Application Data

(60) Provisional application No. 62/865,605, filed on Jun. 24, 2019.

(51) Int. Cl.

| | |
|---|---|
| *C07C 2/12* | (2006.01) |
| *C07C 1/24* | (2006.01) |
| *B01J 38/12* | (2006.01) |
| *B01J 29/70* | (2006.01) |
| *B01J 29/90* | (2006.01) |

(Continued)

(52) U.S. Cl.
CPC .............. *C07C 2/12* (2013.01); *B01J 19/0013* (2013.01); *B01J 19/245* (2013.01); *B01J 29/703* (2013.01); *B01J 29/90* (2013.01); *B01J 38/12* (2013.01); *C01B 3/26* (2013.01); *C07C 1/24* (2013.01); *C07C 29/1518* (2013.01); *B01J 2219/0004* (2013.01); *B01J 2219/00128* (2013.01); *C01B 2203/0233* (2013.01); *C01B 2203/0238* (2013.01); *C01B 2203/061* (2013.01); *C01B 2203/062* (2013.01); *C01B 2203/1241* (2013.01); *C07C 2529/70* (2013.01)

(58) Field of Classification Search
CPC ......... C07C 29/1518; C07C 1/20; C07C 2/12; C07C 31/04; C07C 11/02; C07C 11/06; C07C 2529/70; C07C 31/02; C07C 31/08; C07C 31/10; C07C 9/14; C07C 1/24; C07C 2529/40; C10G 3/49; C10G 50/00; C10G 2400/02; C10G 2400/20; B01J 19/0013; B01J 19/245; B01J 2219/0004; B01J 2219/00128; B01J 29/703; B01J 29/90; B01J 38/02; B01J 38/12; B01J 8/04

See application file for complete search history.

(56) References Cited

U.S. PATENT DOCUMENTS

| 7,183,328 B2 | 2/2007 | Hershkowitz et al. |
| 2017/0121237 A1* | 5/2017 | Ilias .......................... C07C 1/20 |

* cited by examiner

*Primary Examiner* — Sharon Pregler
(74) *Attorney, Agent, or Firm* — Liza Negron

(57) ABSTRACT

Systems and methods are provided for upgrading of methane and/or small alkanes to distillate boiling range hydrocarbons. The upgrading is performed using a reaction system where various types of integration are provided from downstream reaction stages to upstream reaction stages. Such integration can include recycle of various reaction products as well as thermal integration. Having a reaction system that begins with reforming of hydrocarbons and finishes with production of distillate can enable unexpected synergies between downstream reaction stages and upstream reaction stages.

20 Claims, 1 Drawing Sheet

(51) Int. Cl.
*B01J 19/24* (2006.01)
*B01J 19/00* (2006.01)
*C01B 3/26* (2006.01)
*C07C 29/151* (2006.01)

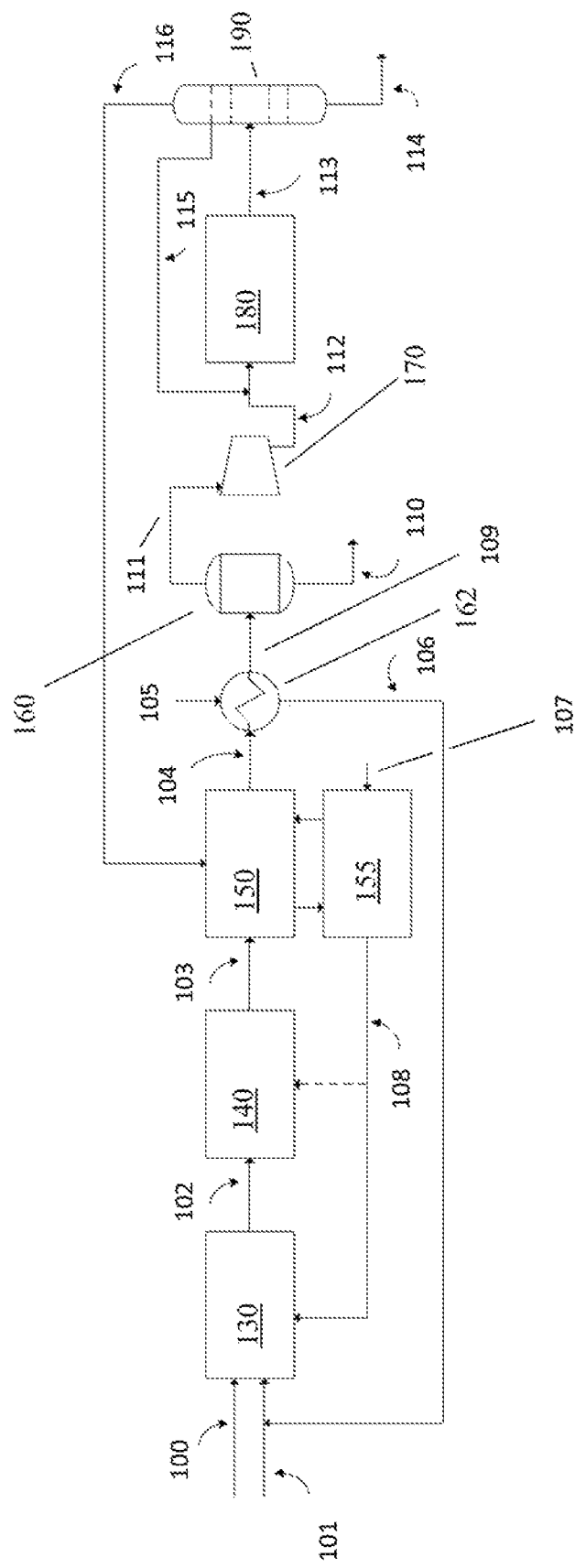

OXYGENATE CONVERSION FOR DISTILLATE FUEL PRODUCTION

CROSS REFERENCE TO RELATED APPLICATIONS

This application claims priority to U.S. Provisional Application Ser. No. 62/865,605 filed Jun. 24, 2019, which is herein incorporated by reference in its entirety.

FIELD

Systems and methods are provided for integrated production of distillate fuels from light hydrocarbon streams via reforming and intermediate olefin production.

BACKGROUND

Natural gas continues to grow in importance as a hydrocarbon resource. While natural gas can be used as a fuel, the value of natural gas could be substantially increased by efficient methods for converting natural gas to larger hydrocarbons, such as distillate fuels.

One of the difficulties in upgrading natural gas is that a majority of the carbon in natural gas corresponds to methane. Methods such as steam cracking can be effective for conversion of $C_{2+}$ alkanes to olefins, but methane is largely unreactive under pyrolysis conditions. Thus, upgrading natural gas can involve methods that allow conversion of methane to larger hydrocarbons and/or hydrocarbon-like compounds.

What is needed are improved methods for conversion of methane and/or natural gas to distillate boiling range hydrocarbons.

U.S. Patent Application Publication 2017/0121237 describes an integrated process for conversion of oxygenates to gasoline and distillates. The integrated process includes conversion of methanol (or another oxygenate) to olefins, and then oligomerization of the olefins to gasoline or distillate fuels. The process is described as performing both the methanol conversion and the oligomerization at similar pressures. This can allow the methanol conversion and oligomerization to optionally be performed in the same reactor.

U.S. Pat. No. 7,183,328 describes a process for conversion of hydrocarbons to methanol via a synthesis gas intermediate. The effluent from a steam reforming process in a pressure swing reactor is used as a synthesis gas feed for methanol synthesis.

SUMMARY

In an aspect, a method for producing distillate boiling range products is provided. The method includes exposing a feed including reformable hydrocarbons and at least one recycle input to a reforming catalyst under reforming conditions to produce a reformed effluent including $H_2$ and CO. At least a portion of the reformed product is exposed to a methanol synthesis catalyst under methanol synthesis conditions to produce a synthesis effluent comprising methanol. A conversion feed including at least a portion of the methanol from the synthesis effluent is then exposed to a conversion catalyst under conversion conditions to form a conversion effluent and to form coke on the conversion catalyst. The conversion effluent can include olefins. At least a portion of the conversion effluent can then be passed into a heat exchange stage to form a cooled conversion effluent and steam. At least a portion of the cooled conversion effluent and a recycled naphtha boiling range feed can be exposed to an oligomerization catalyst under oligomerization conditions to form an oligomerized effluent. A light ends product fraction, a naphtha boiling range product fraction, and a distillate boiling range product fraction can be separated from the oligomerized effluent. The recycled naphtha boiling range feed can include at least a portion of the naphtha boiling range product fraction. Additionally, the coke on at least a portion of the conversion catalyst can be combusted to regenerate the at least a portion of the conversion catalyst and to form a regeneration flue gas comprising $CO_2$. Optionally, the at least one recycle input can include at least a portion of the $CO_2$ from the regeneration flue gas, at least a portion of the steam, or a combination thereof.

In some aspects, exposing at least a portion of the reformed product to a methanol synthesis catalyst can include exposing a combined methanol synthesis feed to the methanol synthesis catalyst. The combined methanol synthesis feed can include the at least a portion of the reformed product and additional $CO_2$. Optionally, the additional $CO_2$ can include a second recycled portion of the $CO_2$ from the regeneration flue gas.

In another aspect, a system for hydrocarbon upgrading is provided. The system can include a reforming reactor, and a methanol synthesis stage in fluid communication with the reforming reactor. The system can further include a conversion reactor including one or more conversion inlets, a conversion outlet, and a conversion catalyst outlet. The conversion reactor can be in fluid communication with the methanol synthesis stage via the one or more conversion inlets. The system can further include a regenerator comprising a regenerator catalyst inlet and a regenerator catalyst outlet. Optionally, the regenerator catalyst outlet can be in fluid communication with the one or more conversion inlets; and/or the regenerator catalyst inlet can be in fluid communication with the conversion catalyst outlet; and/or the regenerator can be further in fluid communication with at least one of the reforming reactor and the methanol synthesis stage via a regenerator recycle outlet. The system can further include an oligomerization reactor comprising an oligomerization inlet and an oligomerization outlet. The oligomerization reactor can be in fluid communication with the conversion outlet via the oligomerization inlet. Additionally, the system can include a separation stage comprising a separator inlet and one or more separator outlets. The separation stage can be in fluid communication with the oligomerization outlet via the separator inlet. Optionally, the separation stage can be in fluid communication with the oligomerization inlet via the one or more separator outlets. Optionally, the separation stage can be further in fluid communication with the one or more conversion inlets via the one or more separator outlets.

BRIEF DESCRIPTION OF THE DRAWINGS

The FIGURE shows an example of a configuration for integrated upgrading of reformable hydrocarbons to distillate boiling range compounds.

DETAILED DESCRIPTION

All numerical values within the detailed description and the claims herein are modified by "about" or "approximately" the indicated value, and take into account experimental error and variations that would be expected by a person having ordinary skill in the art.

Overview

In various aspects, systems and methods are provided for upgrading of methane and/or small alkanes to distillate boiling range hydrocarbons. The upgrading is performed using a reaction system where various types of integration are provided from downstream reaction stages to upstream reaction stages. Such integration can include recycle of various reaction products as well as thermal integration. Having a reaction system that begins with reforming of hydrocarbons and finishes with production of distillate can enable unexpected synergies between downstream reaction stages and upstream reaction stages.

Upgrading of smaller hydrocarbons to larger hydrocarbons is generally desirable from the standpoint of the value for the resulting larger hydrocarbons. Distillate boiling range compounds have a higher value due in part to the ability to use such hydrocarbons in a variety of fuels, as well as other potential uses. However, the conversion of smaller hydrocarbons to larger hydrocarbons often involves substantial costs for equipment as well as operating the equipment at needed processing conditions.

Some efforts to improve upgrading of small hydrocarbons have focused on reforming. Reforming of hydrocarbons is a commonly used technique for generating hydrogen and CO from a hydrocarbon feed. The resulting mixture of hydrogen and CO can then be upgraded in a variety of manners. For example, the resulting mixture of hydrogen and CO can be used as synthesis gas for formation of oxygenates such as methanol and/or dimethyl ether. Although reforming can be performed on a variety of hydrocarbons, reforming of methane is particularly advantageous, due in part to the limited number of other reaction pathways for non-combustion conversion of methane.

Other efforts to improve upgrading of small hydrocarbons have focused on improving upgrading the oxygenates that can be formed by reforming and subsequent synthesis of oxygenates from synthesis gas. One advantage of using synthesis gas to make oxygenates is that a variety of catalysts are available that allow for conversion of oxygenates to olefinic and/or aromatic hydrocarbons. Depending on the selected catalyst, different distributions of olefins, aromatics, and paraffins can be generated. This can allow for flexibility in generating different types of larger hydrocarbon products. In particular, by converting methanol to olefins, the olefins can then be further reacted under oligomerization conditions to form naphtha and/or distillate boiling range compounds.

It has been discovered that additional benefits can be achieved by integrating the upstream process steps of reforming and methanol synthesis with the downstream steps of methanol conversion and olefin oligomerization. Some additional benefits can be related to integration of the methanol conversion step with the upstream process steps. For example, methanol to olefin conversion conditions typically result in formation of coke on the methanol conversion catalyst. During regeneration, the coke on the methanol conversion catalyst can be combusted to form $CO_2$. This $CO_2$ from regeneration of the methanol conversion catalyst can be recycled to the reforming step and/or the methanol synthesis step. If dry or bi-reforming is performed, the recycled $CO_2$ can provide an oxygen source for the dry or bi-reforming reactions. The recycled $CO_2$ can also assist with driving the equilibrium for the water gas shift reaction toward formation of additional CO. The recycled $CO_2$ can similarly be beneficial in the methanol synthesis step for driving equilibrium reactions in a desired direction.

In addition to the above benefits, $CO_2$ recycle also provides an unexpected yield improvement. The coke formed during methanol conversion represents carbon that was originally derived from the hydrocarbon feed. By using the $CO_2$ as a recycle stream for inclusion in the reforming and/or methanol synthesis processes, additional carbon from the original hydrocarbon feed can be incorporated into the final oligomerized products. This can enable generation of additional distillate product yield of 1.0 wt % to 20 wt % relative to the initial weight of hydrocarbons in the hydrocarbon feed to reforming. Additionally, recycling of $CO_2$ for inclusion in the reforming and/or methanol synthesis process can reduce or minimize the amount of $CO_2$ that requires disposal and/or that is exhausted to the environment.

Another example can be heat integration between downstream and upstream processes. Methanol conversion can be performed at relatively low pressure and high temperature. The heated effluent from methanol conversion can be used to raise steam, which can then be recycled as a steam input for steam reforming of hydrocarbons.

Another type of integration can be recycle of one or more portions of the oligomerization effluent to earlier processing steps. For example, at least a portion of the $C_{4-}$ hydrocarbons or the $C_{3-}$ hydrocarbons in the oligomerization effluent can be recycled as a light ends recycle stream for use as part of the feed to the methanol to olefins conversion process. The alkanes in the light ends recycle stream can act as a diluent for the feed, which can be beneficial in view of the exothermic nature of the methanol to olefins conversion reaction. Any olefins in the light ends recycle stream can allow facilitate formation of larger olefins within the methanol to olefins conversion environment.

Additionally or alternately, naphtha boiling range components (roughly $C_4$-$C_8$ or $C_5$-$C_9$) in the oligomerization effluent can be recycled back as part of the input flow to the oligomerization step. Due to the nature of the oligomerization process, the larger hydrocarbons in the oligomerization effluent include a substantial amount of olefins. Recycle of at least a portion of the naphtha boiling range hydrocarbons can allow for further oligomerization in order to increase the yield of the desired distillate boiling range products.

More generally, the systems and methods described herein can allow for increase or maximization of the yield of diesel fuel generated from conversion of oxygenates such as methanol, DME, ethanol, and/or other oxygenates with higher numbers of carbon atoms. This increase in yield can be achieved in part by a two-step process using zeolite catalysts, such as ZSM-48, in both steps. The increase in yield can also be achieved in part through integration of the downstream oxygenate conversion and oligomerization steps with the upstream reforming and oxygenate synthesis steps.

In the initial reforming step, a feed containing reformable hydrocarbons is exposed to reforming conditions. Although methane and/or natural gas are preferred as reformable hydrocarbons, any convenient hydrocarbon that can be reformed to make hydrogen under steam reforming conditions can be used. The reforming conditions can correspond to steam reforming, dry reforming, or bi-reforming conditions. The reforming can convert the reformable hydrocarbons into synthesis gas. The ratio of $H_2$ to CO in the synthesis gas can depend on the nature of the reforming conditions. Preferably, the reforming conditions are suitable for conversion of recycled $CO_2$ to CO, either based on dry reforming or based on the water gas shift reaction.

The synthesis gas can then be passed into a methanol synthesis reactor for methanol production. During methanol synthesis, carbon monoxide and hydrogen can react over a catalyst to produce methanol. Commercial methanol synthesis catalysts can be highly selective, with selectivities of greater than 99.8% possible under optimized reaction conditions. Typical reaction conditions can include pressures of about 5 MPa to about 10 MPa and temperatures of about 250° C. to about 300° C. With regard to the syngas input for methanol synthesis, the preferred ratio of $H_2$ to CO (about 2:1 $H_2$:CO) does not match the typical ratio generated by steam reforming. However, catalysts that facilitate methanol formation from syngas can sometimes additionally facilitate the water-gas shift reaction. As a result, the reaction scheme below shows that $CO_2$ can also be used to form methanol:

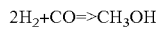

2$H_2$+CO=>$CH_3$OH

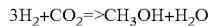

3$H_2$+$CO_2$=>$CH_3$OH+$H_2$O

For methanol synthesis reactions, the composition of the synthesis gas input can be characterized by the Module value M:

M=[$H_2$—$CO_2$]/[CO+$CO_2$]

Module values close to 2 can generally be suitable for production of methanol, such as values of M that are 1.7 or more, or 1.8 or more, or 1.9 or more, and/or 2.3 or less, or 2.2 or less, or 2.1 or less. As can be noted from the Module Value equation above, in addition to the ratio of $H_2$ to CO, the ratio of CO to $CO_2$ in the syngas can impact the reaction rate of the methanol synthesis reaction. Because both CO and $CO_2$ can contribute to methanol synthesis, recycle of $CO_2$ to the methanol synthesis step can allow for additional yield improvement.

With regard to oxygenate conversion, the oxygenate can be converted into intermediate olefins, such as ethylene, propylene, butylene, and/or other olefins with a higher number of carbon atoms. The oxygenate to olefin reaction in the first step also generates significant amount of water from the dehydration reaction. The oxygenate conversion to olefins occurs at relatively low partial pressure of the reactant and high temperature. To prevent the olefins from further reacting during this step, the residence time is relatively short. Due to the highly exothermic nature of the oxygenate to olefin reaction, rigorous heat management is required. Consequently, the catalyst deactivation rate is high and frequent regeneration is required. The intermediate olefin products stream is then cooled down and the water phase is separated from the organic phase. The intermediate olefin products are then pressurized and fed to an oligomerization reactor in the presence of a zeolite catalyst. This reaction occurs at relatively high pressure to allow carbon chain growth and lower temperatures to prevent the longer hydrocarbons from cracking. The reaction is exothermic, therefore, good temperature control and heat management is necessary. The products from the oligomerization reactor are sent to a fractionation tower where the light end gases are sent back to oxygenate to olefin reactor as diluent for controlling the reaction exotherm. Since the oxygenate dehydration reaction occurs at lower pressure than the oligomerization reaction, no compressor for the light end gas recycle is needed. In the fractionation tower, the gasoline range products that are mostly olefinic are removed and recycled back to the oligomerization reactor for two reasons: 1) allow further oligomerization of these heavier olefins to increase diesel yield and 2) to act as diluent and allow better heat management in the reactor. The diesel products are removed at the bottom of the fractionation tower and can be sent to a finishing step, if needed.

In this discussion, a "Tx" distillation point or boiling point for a fraction refers to the weight "x" of the fraction that boils at a specified temperature. Thus, a T90 boiling point or distillation point is the temperature at which 90 wt % of a fraction will boil according to an appropriate test method. For naphtha fractions, D86 is a suitable test method. For distillate fractions, D2887 is suitable test method.

In this discussion, a $C_x$ hydrocarbon refers to a hydrocarbon containing "x" carbon atoms. A "$C_x$ fraction" is defined as a fraction where 50 wt % or more of the fraction corresponds to hydrocarbons, and 70 wt % or more of the hydrocarbons correspond to hydrocarbons containing "x" carbon atoms. A "$C_x$-$C_y$ fraction" is defined as a fraction where 15 wt % or less of the hydrocarbons in the fraction have fewer than "x" hydrocarbons, and 15 wt % or less of the hydrocarbons have more than "y" hydrocarbons.

In this discussion, the naphtha boiling range is defined as starting with the boiling point of $C_5$ hydrocarbons (roughly 30° C.) and ending at roughly 166° C. Due to practical limitations, it is understood that separations based on boiling point are rarely ideal, and therefore a "naphtha boiling range fraction" may include components that boil both above and below the above values. Thus, a naphtha boiling range fraction is defined herein as a fraction with a T10 distillation point (or optionally a T5 distillation point) of 30° C. or more and a T90 distillation point (or optionally a T95 distillation point) of 166° C. or less. Similarly, the distillate boiling range is defined herein as a fraction with a T10 distillation point (or optionally a T5 distillation point) of 166° C. or more and a T90 distillation point (or optionally a T95 distillation point) of 350° C. or less. Hydrocarbons including 4 or fewer carbons can be referred to as $C_{4-}$ compounds. Such $C_{4-}$ hydrocarbons can be considered as light ends or tail gas.

In this discussion, a zeotype is defined to refer to a crystalline material having a porous framework structure built from tetrahedra atoms connected by bridging oxygen atoms. Examples of known zeotype frameworks are given in the "Atlas of Zeolite Frameworks" published on behalf of the Structure Commission of the International Zeolite Association", 6$^{th}$ revised edition, Ch. Baerlocher, L. B. McCusker, D. H. Olson, eds., Elsevier, New York (2007) and the corresponding web site, http://www.iza-structure.org/databases/. Under this definition, a zeotype can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework. Thus, "zeotypes" as defined herein can include structures such as SAPO and AlPO crystalline frameworks.

Configuration Example

The FIGURE shows an example of an integrated system for starting with a reformable hydrocarbon (such as methane or natural gas) and producing a high yield of distillate boiling range products, such as distillate fuels. In the example configuration shown in the FIGURE, a feed 100 (such as natural gas) and steam 101 are sent to a reforming reactor 130 to produce a syngas stream 102 containing CO and $H_2$. The syngas stream is then passed into a methanol synthesis stage 140.

The resulting methanol-containing effluent 103 is then used as feed to the methanol to intermediate olefin (MTiO) reactor 150. The reactor could be multiple fixed bed reactors in series with interstage heat exchangers, or a fluidized bed equipped with cooling coils and a regenerator. The MTiO reactor 150 shown in the FIGURE corresponds to a fluidized bed reactor equipped with cooling coils that also includes an associated regenerator 155. In other aspects, MTiO reactor 150 can correspond to multiple fixed bed reactors in series with interstage heat exchangers. In some aspects, MTiO reactor can be operated at a partial pressure of methanol between 5 psig-20 psig (~35 kPa-g to ~140 kPa-g), or 10 psig-15 psig (~70 kPa-g to ~105 kPa-g). The reaction temperature can be between 350° C.-500° C., or 380° C.-450° C. The weight hourly space velocity (WHSV) can be 0.5 $hr^{-1}$-2 $hr^{-1}$. The reaction is highly exothermic. This is due in part to the substantial amount of water generated as a by-product of the conversion reaction. For instance, in the case of methanol conversion, for every mole of methanol, 2 moles of water are generated. As a result, managing the temperature of the conversion reactor is one of the challenges during operation. In a fixed bed reactor system, heat can be removed via addition of diluent and interstage heat exchangers. The molar ratio of diluent to feed can be between 3.0 to 15 (i.e., 3 to 15 moles of diluent for every mole of methanol or other oxygenate), or between 6.0 to 8.0. In the case of the fluidized bed the exotherm can be managed by heat transfer occurring in the reactor, use of inserted cooling coils, and/or addition of diluent.

The catalyst used in the MTiO reactor 150 can include a zeotype framework structure. Examples of suitable catalysts include, but are not limited to, catalysts having framework types corresponding to MFI (ZSM-5), MEL (ZSM-11), MTW (ZSM-12), TON (ZSM-22), MTT (ZSM-23), FER (ZSM-35), MRE (ZSM-48), and combinations thereof. In some aspects, ZSM-48 can be preferred because it favors formation of heavier ($C_3$-$C_7$) olefins while reducing or minimizing aromatic formation. The heavier olefins formed by using ZSM-48 can reduce the number of oligomerization reactions that are needed to form oligomerized products containing 9 or more carbons, which correspond to the desired distillate boiling range products. Methanol conversion in this reaction can be between 95-100% with intermediate olefin yield up to 40% (on a hydrocarbon basis, excluding any water produced).

The catalyst in the MTiO reaction can deactivate relatively quickly, on a time scale between a few seconds up to roughly 15 days. As a result, the catalyst can benefit from frequent regeneration, such as performing a combustion reaction to burn off the deposited coke by introducing air 107 into the reactor 150 (if fixed bed) or introducing air into regenerator 155 (for fluidized bed or other reactor where catalyst can be readily withdrawn). If the MTiO is a fixed bed reactor system then the regeneration can be either a semi-regeneration or cyclic regeneration mode. In such aspects, one or more reactors are isolated and prepared for regeneration while one or more other reactors remain online to continue providing methanol conversion. If the MTiO reactor 150 is a fluidized bed, then a dedicated regenerator 155 can be used, and air 107 can be (for example) sparged at the bottom of regenerator 155 to fluidize the coked particles and burn the coke. During this regeneration, $CO_2$ is formed by combustion of coke. If separated from the flue gas, this $CO_2$ can be recycled 108 to reforming reactor 130 for use in the reforming step as a bi-reforming agent and/or to methanol synthesis stage 140 for used in the methanol synthesis reaction 108 to increase the efficiency of the overall process.

The intermediate olefin products effluent 104 can be cooled in a heat exchanger, such as a waste heat boiler 162. A waste heat boiler 162 can make high pressure steam 106, which can then be used in the reforming step upstream. The cooled intermediate olefins stream 109 are then sent to a separation stage 160, such as a flash drum, where water 110 is removed. The dried intermediate olefins 111 are then pressurized using a compressor 170 prior to passing the pressurized intermediate olefins 112 into the olefin oligomerization reactor 180. In the example shown in the FIGURE, the olefin oligomerization reactor corresponds to multistage fixed bed reactors with interstage heat exchangers. Using multiple stages of fixed bed reactors of oligomerization can be beneficial for several reasons. First, the rate of catalyst deactivation during oligomerization is relatively slow, and is on the order of 6 months or more. Second, the oligomerization reaction makes products that are liquid phase. Third, the oligomerization reaction can be operated at relatively high pressure. Alternatively, the olefin oligomerization reactor can correspond to a fluidized bed reactor. It is noted that if the same catalyst is used in olefin oligomerization reactor 180 and MTiO reactor 150, the same regenerator 155 can optionally be used to provide regenerated catalyst to both reactors.

The catalyst used in the olefin oligomerization reactor 180 can include a zeotype framework structure. Examples of suitable catalysts include, but are not limited to, catalysts having framework types corresponding to MFI (ZSM-5), MEL (ZSM-11), MTW (ZSM-12), TON (ZSM-22), MTT (ZSM-23), FER (ZSM-35), MRE (ZSM-48), and combinations thereof. The oligomerization reaction is also exothermic, so heat removal can be beneficial to prevent side reactions such as cracking. The reaction pressure can range from 500 to 1000 psig, preferably between 600-850 psig. The temperature can range from 150° C.-300° C., or 180° C.-250° C. The WHSV can range from 0.5 $hr^{-1}$-2 $hr^{-1}$, or 1.0 $hr^{-1}$-1.6 $hr^{-1}$. Intermediate olefin conversion can be between 90-100%.

The effluent 113 from the oligomerization reactor 180 is then sent to a fractionation tower 190. Fractionation tower 190 can separate a plurality of products from the oligomerization effluent 113, including light end gases 116, a naphtha boiling range fraction 115, and a distillate boiling range fraction 114. The light end gases 116 are removed at the top and can be sent to the MTiO reactor 150 as diluent for heat management. Any olefins present in light end gases 116 can also react under the conversion conditions and/or can be passed into the oligomerization reactor. Due to the pressure difference between the oligomerization reactor 180 and the MTiO reactor 150, the light end gases 116 can be recycled back to the MTiO reactor 150 without requiring intermediate compression. The naphtha boiling range products 115 correspond to a $C_4$-$C_8$ hydrocarbon stream that includes a substantial portion of olefinic hydrocarbons. After removing the naphtha boiling range products 115 from the fractionation tower 190, at least a portion can be recycled back to the oligomerization reactor 180 to allow further oligomerization of the naphtha boiling range olefins to distillate compounds and/or to act as a diluent for heat management. An additional portion can be withdrawn as a reaction product. The distillate boiling range fraction 114 can be removed at the bottom of the fractionation tower 190 as a reaction product. Depending on the nature of the catalysts and other reaction conditions, the ratio of distillate boiling range product yield to naphtha boiling range product yield can be between 60/40 to 90/10.

The configuration shown in the FIGURE represents various types of fluid communication between process elements. For example, reforming reactor 130 is shown in the FIGURE as being in direct fluid communication with methanol synthesis stage 140. Such fluid communication can be provided, for example, between a reforming effluent outlet and a synthesis stage inlet. Reforming reactor 130 is also shown as being in indirect fluid communication with conversion reactor 150 via methanol synthesis stage 140.

Additional Processing Conditions—Reforming

The reforming reaction performed within a reforming stage can correspond to reforming of methane and/or other hydrocarbons using steam reforming, in the presence of $H_2O$; using dry reforming, in the presence of $CO_2$; or using "bi" reforming in the presence of both $H_2O$ and $CO_2$. Examples of stoichiometry for steam, dry, and "bi" reforming of methane are shown in equations (1)-(3).

$$\text{Dry Reforming:} CH_4+CO_2=2CO+2H_2 \quad (1)$$

$$\text{Steam Reforming:} CH_4+H_2O=CO+3H_2 \quad (2)$$

$$\text{Bi Reforming:} 3CH_4+2H_2O+CO_2=4CO+8H_2. \quad (3)$$

As shown in equations (1)-(3), dry reforming can produce lower ratios of $H_2$ to CO than steam reforming. Reforming reactions performed with only steam can generally produce a ratio of $H_2$ to CO of around 3, such as 2.5 to 3.5. By contrast, reforming reactions performed in the presence of $CO_2$ can generate much lower ratios, possibly approaching a ratio of $H_2$ to CO of roughly 1.0 or even lower. By using a combination of $CO_2$ and $H_2O$ during reforming, the reforming reaction can potentially be controlled to generate a wide variety of $H_2$ to CO ratios in a resulting syngas.

It is noted that the ratio of $H_2$ to CO in a synthesis gas can also be dependent on the water gas shift equilibrium. Although the above stoichiometry shows ratios of roughly 1 or roughly 3 for dry reforming and steam reforming, respectively, the equilibrium amounts of $H_2$ and CO in a synthesis gas can be different from the reaction stoichiometry. The equilibrium amounts can be determined based on the water gas shift equilibrium, which relates the concentrations of $H_2$, CO, $CO_2$ and $H_2O$ based on the reaction $$H_2O+CO<=>H_2+CO_2 \quad (4)$$

Most reforming catalysts, such as rhodium and/or nickel, can also serve as water gas shift catalysts. Thus, if reaction environment for producing $H_2$ and CO also includes $H_2O$ and/or $CO_2$, the initial stoichiometry from the reforming reaction may be altered based on the water gas shift equilibrium. This equilibrium is also temperature dependent, with higher temperatures favoring production of CO and $H_2O$. It is noted that higher temperatures can also improve the rate for reaching equilibrium. As a result, the ability to perform a reforming reaction at elevated temperatures can potentially provide several benefits. For example, instead of performing steam reforming in an environment with excess $H_2O$, $CO_2$ can be added to the reaction environment. This can allow for both a reduction in the ratio of $H_2$ to CO produced based on the dry reforming stoichiometry as well as a reduction in the ratio of $H_2$ to CO produced based on the water gas shift equilibrium. Alternatively, if a higher $H_2$ to CO ratio is desired, $CO_2$ can be removed from the environment, and the ratio of $H_2O$ to $CH_4$ (or other hydrocarbons) can be controlled to produce a desirable type of synthesis gas. This can potentially allow for generation of a synthesis gas having a $H_2$ to CO ratio of 0.1 to 15, or 0.1 to 3.0, or 0.5 to 5.0, or 1.0 to 10, by selecting appropriate amounts of feed components.

The reforming reactions shown in equations (1)-(3) are endothermic reactions. One of the challenges in commercial scale reforming can be providing the heat for performing the reforming reaction in an efficient manner while reducing or minimizing introduction of additional components into the desired synthesis gas product. Cyclic reaction systems, such as reverse flow reactor systems, can provide heat in a desirable manner by having a cycle including a reforming step and a regeneration step. During the regeneration step, combustion can be performed within a selected area of the reactor. A gas flow during regeneration can assist with transferring this heat from the combustion zone toward additional portions of the reforming zone in the reactor. The reforming step within the cycle can be a separate step, so that incorporation of products from combustion into the reactants and/or products from reforming can be reduced or minimized. The reforming step can consume heat, which can reduce the temperature of the reforming zone. As the products from reforming pass through the reactor, the reforming products can pass through a second zone that lacks a reforming or water gas shift catalyst. This can allow the reaction products to cool prior to exiting the reactor. The heat transferred from the reforming products to the reactor can then be used to increase the temperature of the reactants for the next combustion or regeneration step.

One common source for methane is natural gas. In some applications, natural gas, including associated hydrocarbon and impurity gases, may be used as a feed for the reforming reaction. The supplied natural gas also may be sweetened and/or dehydrated natural gas. Natural gas commonly includes various concentrations of associated gases, such as ethane and other alkanes, preferably in lesser concentrations than methane. The supplied natural gas may include impurities, such as $H_2S$ and nitrogen. More generally, the hydrocarbon feed for reforming can include any convenient combination of methane and/or other hydrocarbons. Optionally, the reforming feed may also include some hydrocarbonaceous compounds, such as alcohols or mercaptans, which are similar to hydrocarbons but include one or more heteroatoms different from carbon and hydrogen. In some aspects, an additional component present in the feed can correspond to impurities such as sulfur that can adsorb to the catalytic monolith during a reducing cycle (such as a reforming cycle). Such impurities can be oxidized in a subsequent cycle to form sulfur oxide, which can then be reduced to release additional sulfur-containing components (or other impurity-containing components) into the reaction environment.

In some aspects, the feed for reforming can include, relative to a total weight of hydrocarbons in the feed for reforming, 5 wt % or more of $C_{2+}$ compounds, such as ethane or propane, or 10 wt % or more, or 15 wt % or more, or 20 wt % or more, such as up to 50 wt % or possibly still higher. It is noted that nitrogen and/or other gases that are non-reactive in a combustion environment, such as $H_2O$ and $CO_2$, may also be present in the feed for reforming. In aspects where the reformer corresponds to an on-board reforming environment, such non-reactive products can optionally be introduced into the feed, for example, based on recycle of an exhaust gas into the reformer. Additionally or alternately, the feed for reforming can include 40 wt % or more methane, or 60 wt % or more, or 80 wt % or more, or 95 wt % or more, such as having a feed that is substantially composed of methane (98 wt % or more). In aspects where the reforming corresponds to steam reforming, a molar ratio of steam molecules to carbon atoms in the feed can be 0.3 to 4.0. It is noted that methane has 1 carbon atom per molecule while ethane has 2 carbon atoms per molecule. In aspects where the reforming corresponds to dry reforming, a molar ratio of $CO_2$ molecules to carbon atoms in the feed can be 0.05 to 3.0.

The temperature within a reforming reactor can be 600° C. or greater. For example, the temperature can be 600° C. to 1500° C., or 800° C. to 1500° C., or 600° C. to 1000° C., or 800° C. to 1200° C. In addition to conventional reforming reactor designs, reforming can also be performed in a reverse flow reactor. The reaction conditions for reforming hydrocarbons can also include a pressure of 0 psig to 1500 psig (10.3 MPa), or 0 psig to 1000 psig (6.9 MPa), or 0 psig to 550 psig (3.8 MPa).

In some aspects, an advantage of operating the reforming reaction at elevated temperature can be the ability to convert substantially all of the methane and/or other hydrocarbons in a reforming feed. For example, for a reforming process where water is present in the reforming reaction environment (i.e., steam reforming or bi-reforming), the reaction conditions can be suitable for conversion of 10 wt % to 100 wt % of the methane in the reforming feed, or 20 wt % to 80 wt %, or 50 wt % to 100 wt %, or 80 wt % to 100 wt %, or 10 wt % to 98 wt %, or 50 wt % to 98 wt %. Additionally or alternately, the reaction conditions can be suitable for conversion of 10 wt % to 100 wt % of the hydrocarbons in the reforming feed, or 20 wt % to 80 wt %, or 50 wt % to 100 wt %, or 80 wt % to 100 wt %, or 10 wt % to 98 wt %, or 50 wt % to 98 wt %

In other aspects, for a reforming process where carbon dioxide is present in the reforming reaction environment (i.e., dry reforming or bi-reforming), the reaction conditions can be suitable for conversion of 10 wt % to 100 wt % of the methane in the reforming feed, or 20 wt % to 80 wt %, or 50 wt % to 100 wt %, or 80 wt % to 100 wt %, or 10 wt % to 98 wt %, or 50 wt % to 98 wt %. Additionally or alternately, the reaction conditions can be suitable for conversion of 10 wt % to 100 wt % of the hydrocarbons in the reforming feed, or 20 wt % to 80 wt %, or 50 wt % to 100 wt %, or 80 wt % to 100 wt %, or 10 wt % to 98 wt %, or 50 wt % to 98 wt %.

Additional Processing Conditions—Methanol Synthesis

The syngas produced in the reforming stage can be sent to a methanol synthesis process and converted to methanol. The methanol synthesis process is accomplished in the presence of a methanol synthesis catalyst.

In one embodiment, the syngas is sent as is to the methanol synthesis process. In another embodiment, the hydrogen, carbon monoxide, and/or carbon dioxide content of the syngas is adjusted for efficiency of conversion. Desirably, the syngas input to the methanol synthesis reactor has a molar ratio of hydrogen ($H_2$) to carbon oxides (CO+$CO_2$) in the range of from about 0.5:1 to about 20:1, preferably in the range of from about 2:1 to about 10:1. In another embodiment, the syngas has a molar ratio of hydrogen ($H_2$) to carbon monoxide (CO) of at least 2:1. Carbon dioxide is optionally present in an amount of not greater than 50% by weight, based on total weight of the syngas.

Desirably, the stoichiometric molar ratio is sufficiently high so as maintain a high yield of methanol, but not so high as to reduce the volume productivity of methanol. Conveniently, the syngas fed to the methanol synthesis has a stoichiometric molar ratio (i.e., a molar ratio of $H_2$:(2CO+3$CO_2$)) of from about 1.0:1 to about 2.7:1, such as from about 1.1 to about 2.0.

In some aspects, the adjustment of the syngas can be based on addition of $CO_2$ that is recycled from regeneration of the methanol conversion catalyst. The $CO_2$ can be added to adjust the value of the module M so that M is 1.7 or more, or 1.8 or more, or 1.9 or more, and/or 2.3 or less, or 2.2 or less, or 2.1 or less.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide.

In another embodiment, the catalyst used in the methanol synthesis process is a copper based catalyst, which includes an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

In yet another embodiment, the methanol synthesis catalyst comprises copper oxide, zinc oxide, and at least one other oxide. Conveniently, the at least one other oxide is selected from zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, such as from about 15 wt % to about 68 wt % copper oxide, for example from about 20 wt % to about 65 wt % copper oxide based on total weight of the catalyst.

In one embodiment, the methanol synthesis catalyst comprises from about 3 wt % to about 30 wt % zinc oxide, such as from about 4 wt % to about 27 wt % zinc oxide, for example from about 5 wt % to about 24 wt % zinc oxide based on total weight of the catalyst.

In embodiments in which copper oxide and zinc oxide are both present in the methanol synthesis catalyst, the ratio of copper oxide to zinc oxide can vary over a wide range. Typically in such embodiments, the methanol synthesis catalyst comprises copper oxide and zinc oxide in a Cu:Zn atomic ratio of from about 0.5:1 to about 20:1, such as from about 0.7:1 to about 15:1, for example from about 0.8:1 to about 5:1. The methanol synthesis catalyst can be made by any convenient method, such as according to a conventional process.

The methanol synthesis process implemented in the present invention can be any conventional methanol synthesis process. Examples of such processes include batch processes and continuous processes. Continuous processes are preferred. Tubular bed processes and fluidized bed processes are particularly preferred types of continuous processes.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 hr$^{-1}$ to about 50,000 hr$^{-1}$, such as from about 250 hr$^{-1}$ to about 25,000 hr$^{-1}$, more preferably from about 500 hr$^{-1}$ to about 10,000 hr$^{-1}$.

In addition to the desired methanol product, the tail gas from the methanol synthesis process comprises unconverted carbon monoxide, carbon dioxide and hydrogen from the synthesis gas input, and unconverted hydrocarbon from the reformer.

Methanol synthesis is an exothermic process and it is necessary to limit the amount of reaction occurring in a bed of catalyst and/or to cool the bed, to avoid overheating the catalyst. To this end, a variety of reactor types may be employed. For example it is possible to employ a reactor with means to inject cool quench gas (generally a mixture of make-up gas and unreacted recycle gas) into the catalyst bed or between beds. It is also known to employ reactors having heat exchangers within the beds so that heat evolved by the reaction is transferred to a coolant. For example, the synthesis reactor can include coolant tubes which extend through at least the inlet part of the catalyst bed and open into the space above the inlet to the catalyst bed. In such a configuration, the coolant can be a mixture of recycled unreacted gas and make-up gas so that the reactants are heated to the desired inlet temperature by the evolved heat.

Additional Embodiments

Embodiment 1. A method for producing distillate boiling range products, comprising: exposing a feed comprising reformable hydrocarbons and at least one recycle input to a reforming catalyst under reforming conditions to produce a reformed effluent comprising $H_2$ and CO; exposing at least a portion of the reformed product to a methanol synthesis catalyst under methanol synthesis conditions to produce a synthesis effluent comprising methanol; exposing a conversion feed comprising at least a portion of the methanol from the synthesis effluent to a conversion catalyst under conversion conditions to form a conversion effluent comprising olefins and to form coke on the conversion catalyst; passing at least a portion of the conversion effluent into a heat exchange stage to form a cooled conversion effluent and steam; exposing at least a portion of the cooled conversion effluent and a recycled naphtha boiling range feed to an oligomerization catalyst under oligomerization conditions to form an oligomerized effluent; separating a light ends product fraction, a naphtha boiling range product fraction, and a distillate boiling range product fraction from the oligomerized effluent, the recycled naphtha boiling range feed comprising at least a portion of the naphtha boiling range product fraction; and combusting the coke on at least a portion of the conversion catalyst to regenerate the at least a portion of the conversion catalyst and to form a regeneration flue gas comprising $CO_2$, wherein the at least one recycle input comprises at least a portion of the $CO_2$ from the regeneration flue gas, at least a portion of the steam, or a combination thereof.

Embodiment 2. The method of Embodiment 1, wherein exposing at least a portion of the reformed product to a methanol synthesis catalyst comprises exposing a combined methanol synthesis feed to the methanol synthesis catalyst, the combined methanol synthesis feed comprising the at least a portion of the reformed product and additional $CO_2$, the additional $CO_2$ comprising a second recycled portion of the $CO_2$ from the regeneration flue gas.

Embodiment 3. The method of any of the above embodiments, wherein a module M of the reformed product is 1.7 to 3.0, or wherein a Module M of the combined methanol synthesis feed is 1.7 to 2.3, or a combination thereof.

Embodiment 4. The method of any of the above embodiments, wherein the conversion feed further comprises at least a portion of the light ends product fraction.

Embodiment 5. The method of Embodiment 4, wherein the at least a portion of the light ends product fraction is included in the conversion feed without compression of the light ends product fraction or the at least a portion of the light ends product fraction.

Embodiment 6. The method of any of the above embodiments, wherein the conversion conditions comprise fluidized bed conversion conditions, and wherein combusting the coke on the at least a portion of the conversion catalyst comprises: transferring the at least a portion of the conversion catalyst from a conversion reactor to a regenerator; and combusting the coke on the at least a portion of the conversion catalyst in the regenerator.

Embodiment 7. The method of any of the above embodiments, i) wherein the conversion catalyst comprises a zeotype framework structure selected from MFI, MEL, MTW, TON, MTT, FER, MRE, and combinations thereof, ii) wherein the oligomerization catalyst comprises a zeotype framework structure selected from MFI, MEL, MTW, TON, MTT, FER, MRE, and combinations thereof; or iii) a combination of i) and ii).

Embodiment 8. The method of any of the above embodiments, wherein at least one of the conversion catalyst and the oligomerization catalyst comprise ZSM-48, or wherein the conversion catalyst and the oligomerization catalyst are the same catalyst, or a combination thereof.

Embodiment 9. The method of any of the above embodiments, wherein the reformable hydrocarbons comprise methane, natural gas, or a combination thereof.

Embodiment 10. The method of any of the above embodiments, wherein the reforming conditions comprise steam reforming, dry reforming, or a combination thereof.

Embodiment 11. The method of any of the above embodiments, wherein the light ends product fraction comprises $C_{3-}$ hydrocarbons, or wherein the naphtha boiling range product fraction comprises $C_4$-$C_8$ hydrocarbons, or a combination thereof; or wherein the light ends product fraction comprises $C_{4-}$ hydrocarbons, or wherein the naphtha boiling range product fraction comprises $C_5$-$C_9$ hydrocarbons, or a combination thereof.

Embodiment 12. The method of any of the above embodiments, wherein 1.0 wt % to 20 wt % of the distillate yield corresponds to distillate yield generated based on recycle of $CO_2$ as part of the at least one recycle input, recycle of $CO_2$ as part of the additional $CO_2$, or a combination thereof.

Embodiment 13. A system for hydrocarbon upgrading comprising: a reforming reactor; a methanol synthesis stage in fluid communication with the reforming reactor; a conversion reactor comprising one or more conversion inlets, a conversion outlet, and a conversion catalyst outlet, the conversion reactor being in fluid communication with the methanol synthesis stage via the one or more conversion inlets; a regenerator comprising a regenerator catalyst inlet and a regenerator catalyst outlet, the regenerator catalyst outlet being in fluid communication with the one or more conversion inlets, the regenerator catalyst inlet being in fluid communication with the conversion catalyst outlet, the regenerator being further in fluid communication with at least one of the reforming reactor and the methanol synthesis stage via a regenerator recycle outlet; an oligomerization reactor comprising an oligomerization inlet and an oligomerization outlet, the oligomerization reactor being in fluid communication with the conversion outlet via the oligomerization inlet; and a separation stage comprising a separator inlet and one or more separator outlets, the separation stage being in fluid communication with the oligomerization outlet via the separator inlet, the separation stage being in fluid communication with the oligomerization inlet via the one or more separator outlets, the separation stage being further in fluid communication with the one or more conversion inlets via the one or more separator outlets.

Embodiment 14. The system of Embodiment 13, the system further comprising a waste heat boiler, the conversion reactor outlet being in indirect fluid communication with the oligomerization inlet via the waste heat boiler, wherein the waste heat boiler comprises a steam outlet, the steam outlet being in fluid communication with the reforming reactor.

Embodiment 15. A distillate boiling range product produced by the method of any of Embodiments 1-12 or by the system of any of Embodiments 13-14.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for producing distillate boiling range products, comprising:
exposing a feed comprising reformable hydrocarbons and at least one recycle input to a reforming catalyst under reforming conditions to produce a reformed effluent comprising $H_2$ and CO;
exposing at least a portion of the reformed product to a methanol synthesis catalyst under methanol synthesis conditions to produce a synthesis effluent comprising methanol;
exposing a conversion feed comprising at least a portion of the methanol from the synthesis effluent to a conversion catalyst under conversion conditions to form a conversion effluent comprising olefins and to form coke on the conversion catalyst;
passing at least a portion of the conversion effluent into a heat exchange stage to form a cooled conversion effluent and steam;
exposing at least a portion of the cooled conversion effluent and a recycled naphtha boiling range feed to an oligomerization catalyst under oligomerization conditions to form an oligomerized effluent;
separating a light ends product fraction, a naphtha boiling range product fraction, and a distillate boiling range product fraction from the oligomerized effluent, the recycled naphtha boiling range feed comprising at least a portion of the naphtha boiling range product fraction; and
combusting the coke on at least a portion of the conversion catalyst to regenerate the at least a portion of the conversion catalyst and to form a regeneration flue gas comprising $CO_2$,
wherein the at least one recycle input comprises at least a portion of the $CO_2$ from the regeneration flue gas, at least a portion of the steam, or a combination thereof.

2. The method of claim 1, wherein exposing at least a portion of the reformed product to a methanol synthesis catalyst comprises exposing a combined methanol synthesis feed to the methanol synthesis catalyst, the combined methanol synthesis feed comprising the at least a portion of the reformed product and additional $CO_2$.

3. The method of claim 2, wherein the additional $CO_2$ comprises a second recycled portion of the $CO_2$ from the regeneration flue gas.

4. The method of claim 2, wherein the at least one recycle input comprises the at least a portion of the $CO_2$ from the regeneration flue gas.

5. The method of claim 1, wherein a module M of the reformed product is 1.7 to 3.0.

6. The method of claim 2, wherein a Module M of the combined methanol synthesis feed is 1.7 to 2.3.

7. The method of claim 1, wherein the conversion feed further comprises at least a portion of the light ends product fraction.

8. The method of claim 7, wherein the at least a portion of the light ends product fraction is included in the conversion feed without compression of the light ends product fraction or the at least a portion of the light ends product fraction.

9. The method of claim 1, wherein the conversion conditions comprise fluidized bed conversion conditions, and wherein combusting the coke on the at least a portion of the conversion catalyst comprises:
transferring the at least a portion of the conversion catalyst from a conversion reactor to a regenerator; and
combusting the coke on the at least a portion of the conversion catalyst in the regenerator.

10. The method of claim 1, wherein the conversion catalyst comprises a zeotype framework structure selected from MFI, MEL, MTW, TON, MTT, FER, MRE, and combinations thereof.

11. The method of claim 1, wherein the oligomerization catalyst comprises a zeotype framework structure selected from MFI, MEL, MTW, TON, MTT, FER, MRE, and combinations thereof.

12. The method of claim 1, wherein at least one of the conversion catalyst and the oligomerization catalyst comprise ZSM-48, or wherein the conversion catalyst and the oligomerization catalyst are the same catalyst, or a combination thereof.

13. The method of claim 1, wherein the reformable hydrocarbons comprise methane, natural gas, or a combination thereof.

14. The method of claim 1, wherein the reforming conditions comprise steam reforming, dry reforming, or a combination thereof.

15. The method of claim 1, wherein the light ends product fraction comprises $C_{3-}$ hydrocarbons, or wherein the naphtha boiling range product fraction comprises $C_4$-$C_8$ hydrocarbons, or a combination thereof.

16. The method of claim 1, wherein the light ends product fraction comprises $C_{4-}$ hydrocarbons, or wherein the naphtha boiling range product fraction comprises $C_5$-$C_9$ hydrocarbons, or a combination thereof.

17. The method of claim 1, wherein 1.0 wt % to 20 wt % of the distillate yield corresponds to distillate yield generated based on recycle of $CO_2$ as part of the at least one recycle input, recycle of $CO_2$ as part of the additional $CO_2$, or a combination thereof.

18. A system for hydrocarbon upgrading comprising:
a reforming reactor;
a methanol synthesis stage in fluid communication with the reforming reactor;
a conversion reactor comprising one or more conversion inlets, a conversion outlet, and a conversion catalyst outlet, the conversion reactor being in fluid communication with the methanol synthesis stage via the one or more conversion inlets;

a regenerator comprising a regenerator catalyst inlet and a regenerator catalyst outlet, the regenerator catalyst outlet being in fluid communication with the one or more conversion inlets, the regenerator catalyst inlet being in fluid communication with the conversion catalyst outlet, the regenerator being further in fluid communication with at least one of the reforming reactor and the methanol synthesis stage via a regenerator recycle outlet;

an oligomerization reactor comprising an oligomerization inlet and an oligomerization outlet, the oligomerization reactor being in fluid communication with the conversion outlet via the oligomerization inlet; and a separation stage comprising a separator inlet and one or more separator outlets, the separation stage being in fluid communication with the oligomerization outlet via the separator inlet, the separation stage being in fluid communication with the oligomerization inlet via the one or more separator outlets, the separation stage being further in fluid communication with the one or more conversion inlets via the one or more separator outlets.

19. The system of claim 18, the system further comprising a waste heat boiler, the conversion reactor outlet being in indirect fluid communication with the oligomerization inlet via the waste heat boiler.

20. The system of claim 19, wherein the waste heat boiler comprises a steam outlet, the steam outlet being in fluid communication with the reforming reactor.

* * * * *